United States Patent
Buffa et al.

(10) Patent No.: US 11,425,907 B2
(45) Date of Patent: *Aug. 30, 2022

(54) COMPOSITION COMPRISING AN IODIDE AND A DERIVATIVE OF HYALURONIC ACID WITH AN OXIDATIVE EFFECT, METHOD OF PREPARATION THEREOF AND USE THEREOF

(71) Applicant: CONTIPRO A.S., Dolni Dobrouc (CZ)

(72) Inventors: Radovan Buffa, Humenne (SK); Vit Svozil, Usti nad Orlici (CZ); Katerina Knotkova, Chocen (CZ); Veronika Stepankova, Litomysl (CZ); Jaromir Kulhanek, Pardubice (CZ); Josef Chmelar, Hylvaty (CZ); Lucie Marholdova, Chocen (CZ); Ivana Basarabova, Medzilaborce (SK); Michaela Moravkova, Zamberk (CZ); Helena Krejci, Svitavy (CZ); Kristyna Lipenska, Letohrad (CZ); Jaroslav Novotny, Letohrad (CZ); Stanislav Pepeliaev, Ceska Trebova (CZ); Lubos Sobotka, Malsovice (CZ); Vladimir Velebny, Zamberk (CZ)

(73) Assignee: CONTIPRO A.S., Dolni Dobrouc (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/270,617

(22) PCT Filed: Aug. 17, 2019

(86) PCT No.: PCT/CZ2019/050035
§ 371 (c)(1),
(2) Date: Feb. 23, 2021

(87) PCT Pub. No.: WO2020/038501
PCT Pub. Date: Feb. 27, 2020

(65) Prior Publication Data
US 2021/0345610 A1    Nov. 11, 2021

(30) Foreign Application Priority Data
Aug. 23, 2018    (CZ) .............................. CZ2018-428

(51) Int. Cl.
| A01N 43/16 | (2006.01) |
| A01N 25/04 | (2006.01) |
| A01N 25/08 | (2006.01) |
| A01N 59/12 | (2006.01) |
| C08B 37/08 | (2006.01) |
| A61K 31/728 | (2006.01) |
| A61L 15/28 | (2006.01) |
| A61P 31/04 | (2006.01) |
| A61L 27/20 | (2006.01) |

(52) U.S. Cl.
CPC ............. *A01N 43/16* (2013.01); *A01N 25/04* (2013.01); *A01N 25/08* (2013.01); *A01N 59/12* (2013.01); *A61K 31/728* (2013.01); *A61L 15/28* (2013.01); *A61L 27/20* (2013.01); *A61P 31/04* (2018.01); *C08B 37/0072* (2013.01)

(58) Field of Classification Search
CPC .. C08B 37/0072; A61K 31/728; A61K 33/18; A61P 31/04; A61L 15/28; A61L 27/20; A01N 59/08; A01N 59/12
See application file for complete search history.

(56) References Cited

U.S. PATENT DOCUMENTS

2005/0181025 A1    8/2005    Velebny et al.

FOREIGN PATENT DOCUMENTS

| CZ | 12015 U1 | 2/2002 | |
| CZ | 2009399 A3 | 1/2011 | |
| CZ | 22394 U1 | 6/2011 | |
| CZ | 303548 B6 | 10/2012 | |
| CZ | 2013913 A3 | 6/2015 | |
| CZ | 2015166 A3 | 9/2016 | |
| CZ | 306354 B6 | 11/2016 | |
| CZ | 308010 B6 | 9/2019 | |
| EP | 2925916 B1 | 8/2019 | |
| WO | 0248197 A1 | 6/2002 | |
| WO | WO-2008094664 A1 * | 8/2008 | .............. A61P 25/00 |
| WO | 2010105582 A1 | 9/2010 | |
| WO | 2011069475 A2 | 6/2011 | |
| WO | 2012092908 A1 | 7/2012 | |
| WO | WO-2015074631 A * | 5/2015 | ............... D01F 9/00 |

OTHER PUBLICATIONS

Akeel A, et al., Chlorination and oxidation of heparin and hyaluronan by hypochlorous acid and hypochlorite anions: effect of sulfate groups on reaction pathways and kinetics. Free Radic Biol Med. Mar. 2013;56:72-88.

(Continued)

*Primary Examiner* — Leigh C Maier
(74) *Attorney, Agent, or Firm* — Lorenz & Kopf LLP

(57) ABSTRACT

An antimicrobial composition is provided. The composition comprises a chloramid of hyaluronic acid or of modified hyaluronic acid. The chloramid has an amidic group (—NH—CO—). The hydrogens of the amidic group are substituted by chlorine atoms according to the structural formula —NCl—CO—. The composition further comprises an iodide. The substitution degree of the hyaluronic acid or of the modified hyaluronic acid by chlorine is in an amount of from 50% to 100%.

11 Claims, 2 Drawing Sheets

(56) References Cited

OTHER PUBLICATIONS

Baker MS, et al., Changes in the viscosity of hyaluronic acid after exposure to a myeloperoxidase-derived oxidant. Arthritis Rheum. Apr. 1989.;32(4):461-7.
Bezdekova, B. et al., Veterinarstvi 54, 516-519, 2004, abstract only.
Burdick, J. et al., Hyaluronic acid hydrogels for biomedical applications. Adv Mater. Mar. 25, 2011;23(12):H41-56.
Cao, Z. et al. Polymeric N-halamine latex emulsions for use in antimicrobial paints. ACS Appl Mater Interfaces. Feb. 2009;1(2)1494-504.
Cutting KF. Wound healing through synergy of hyaluronan and an iodine complex. J Wound Care. Sep. 2011;20(9):424, 426, 428-30.
Foglarova, M., et al. Water-insoluble thin films from palmitoyl hyaluronan with tunable properties. Carbohydrate Polymers, 144, Feb. 2016.:69-75.
Frankova, J., et al. The effect of hyaluronan combined with KI3 complex (Hyiodine wound dressing) on keratinocytes and immune cells. J Mater Sci: Mater Med 17, 891-898 (2006).
Green SP, et al., Depolymerization of synovial fluid hyaluronic acid (HA) by the complete myeloperoxidase (MPO) system may involve the formation of a HA-MPO ionic complex. J Rheumatol. Dec. 1990;17(12):1670-5, abstract only.
Hawkins CL, et al., Degradation of hyaluronic acid, poly- and monosaccharides, and model compounds by hypochlorite: evidence for radical intermediates and fragmentation. Free Radic Biol Med. Jun. 1998;24(9):1396-410.
Hiegel, GA, et al.. Preparation of N-Chloroamides Using Trichloroisocyanuric Acid. Synthetic Communications, 35. Apr. 2005, 2099-2105.
Lindvall, S. et al., Influence of various compounds on the degradation of hyaluronic acid by a myeloperoxidase system. Chem Biol Interact. Jan. 1994;90(1):1-12.

Rees MD, et al., Hypochlorite-mediated fragmentation of hyaluronan, chondroitin sulfates, and related N-acetyl glycosamines: evidence for chloramide intermediates, free radical transfer reactions, and site-specific fragmentation. J Am Chem Soc. Nov. 12, 2003;125(45):13719-33.
Rees MD, et al., Hypochlorite and superoxide radicals can act synergistically to induce fragmentation of hyaluronan and chondroitin sulphates. Biochem J. Jul. 1, 2004;381(Pt 1):175-84.
Slavkovsky, R., et al., Effects of hyaluronan and iodine on wound contraction and granulation tissue formation in rat skin wounds. Clin Exp Dermatol. Jun. 2010;35(4):373-9.
Sun, X. et al., Amine, Melamine, and Amide N-Halamines as Antimicrobial Additives for Polymers. Ind Eng Chem Res. 2010;49(22):11206-11213.
Zapotocky, V. et al. Fabrication of biodegradable textile scaffold based on hydrophobized hyaluronic acid. International Journal of Biological Macromolecules. Feb. 2017;95:903-909.
International Search Report and Written Opinion of the International Searching Authority, dated Nov. 13, 2019, for PCT/CZ2019/050035.
Machine translation of CZ12015 obtained from https://patents.google.com on Jun. 28, 2021.
Machine translation of CZ22394 obtained from https://patents.google.com on Jun. 28, 2021.
Machine translation of CZ303548 obtained from https://patents.google.com on Jun. 28, 2021.
Machine translation of CZ306354 obtained from https://patents.google.com on Jun. 28, 2021.
Machine translation of CZ308010 obtained from https://patents.google.com on Jun. 28, 2021.
Machine translation of CZ2009399 obtained from https://patents.google.com on Jun. 28, 2021.
Machine translation of CZ2013913 obtained from https://patents.google.com on Jun. 28, 2021.
Machine translation of CZ2015166 obtained from https://patents.google.com on Jun. 28, 2021.

* cited by examiner

HA Chloramide + KI          control

COMPOSITION COMPRISING AN IODIDE AND A DERIVATIVE OF HYALURONIC ACID WITH AN OXIDATIVE EFFECT, METHOD OF PREPARATION THEREOF AND USE THEREOF

CROSS-REFERENCE TO RELATED APPLICATIONS

This application is the National Stage of International Application No. PCT/CZ2019/050035, filed on 17 Aug. 2019, which claims priority to and all advantages of CZ Application No. PV2018-428, filed on 23 Aug. 2018, both of which are incorporated herein by reference in their entirety.

TECHNICAL FIELD

The invention relates to compositions comprising an iodide and a derivative of hyaluronic acid, also referred to as hyaluronan chloramide, in which the majority of the hydrogen atoms contained in the amidic group —NH—CO— is substituted by chlorine atoms according to the structural formula —NCl—CO—.

BACKGROUND

The Hyaluronic Acid

Hyaluronic acid or the sodium salt thereof is a nonsulfated glycosaminoglycan constituted by two repeating units of D-glucuronic acid and N-acetyl-D-glucosamine.

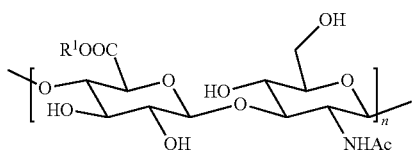

wherein
$R^1$ stands for hydrogen or sodium.

The molecular weight of the native hyaluronic acid ranges between $5.10^4$ and $5.10^6$ g.mol$^{-1}$. This hydrophilic polysaccharide plays a significant role in numerous biological processes, such as hydration, organization of proteoglycans or differentiation of cells, and is known to be an essential constituent of skin, synovial joint fluid and connective tissues. The aforesaid polymer is naturally occurring in biological systems and therefore it can be characterized as being biodegradable and biocompatible. Hence, it makes a suitable substrate in the field of carriers of biologically active substances for a wide range of biomedical applications.

Chemical Modifications and Forms of the Hyaluronic Acid

There are numerous known methods of chemical modifications of hyaluronic acid for the purpose of adjusting the physical and biological properties of the same (Burdick J. A. and Prestwich G. D., Adv. Mater. 23, 41-56, 2011). In case an essential change in solubility is required in connection with a particular application, the most frequently performed procedure consists in covalent linking a hydrophobic chain to the polymeric structure utilizing a biodegradable ester bond (Kettou S. et al., PV 2009-399, Buffa R. et al., WO2010105582). When modified in the above manner, such materials can be used for the preparation of various forms, such as fibres (Scudlova J. et. al., EP2925916 A1), knitted and braided fabrics (Pitucha T. et al., CZ Pat. No. 306354), self-supporting films (Foglarova M. et al. PV2015-166; Foglarova M. Et al., Carbohydrate Polymers, 144, 68-75, 2016) or nanofibrous layers (Ruzickova J. et al. PV2013-913). Non-woven fabrics are formed by combining staple microfibres, the latter being prepared utilizing the wet spinning process in a non-stationary coagulation bath (Zapotocky V. et al., International Journal of Biological Macromolecules, 95, 903-909, 2017).

Oxidation with Trichloroisocyanuric Acid or with Sodium Trichloroisocyanurate

Trichloroisocyanuric acid (TCC) is often used for performing the N-chlorination of structurally simpler amides to N-chloramides (Hiegel G. A. et al., Synthetic Communications, 35, 2099-2105, 2005), mostly in non-aqueous solvents. Furthermore, TCC is often mentioned in combination with stable radicals, such as piperidinyloxy ones (TEMPO), for selectively oxidizing primary hydroxyl groups in the presence of water. In connection with hyaluronic acid, the use of TCC along with TEMPO in water was described, for example, in the patent (Buffa R. et al., WO2011069475A3), where no formation of chloramides but only the oxidation of the primary hydroxyl groups to an aldehyde and carboxylic acid was observed. Hence, in case of substrates containing large amounts of both secondary and primary alcohols (polysaccharides), reactions on hydroxyl groups can be expected when TCC and analogues thereof are used. The monosodium TCC salt, which is also known as sodium dichloroisocyanurate (DCC-Na), is a less reactive but more water soluble analogue of TCC. The use DCC-Na was disclosed for oxidizing several amines and amides which, however, do not contain hydroxyl groups (Sun X. et al., Ind. Eng. Chem. Res., 49, 22, 2010). The resulting chloramines were then polymerized and, subsequently, the final substrates were successfully tested as antibacterial, antifungal and antiviral substances in the form of a latex emulsion (Cao Z. et al., App. Mat. Inter. 1, 2, 494-504, 2009).

On the basis of the above outputs, it can be concluded that the use of TCC or of certain analogues thereof for selective preparation of N-chlorinated hyaluronan amide in water cannot be expected due to the presupposed reaction with the hydroxy groups of hyaluronan.

Oxidation of Polysaccharides with Hypochlorous Acid or with a Hypochlorite

Hypochlorous acid and the salts thereof are often used for the oxidation of hydroxyl groups of polysaccharides, mainly in combination with piperidinyloxy radicals (TEMPO) (Bragd P. et al., WO2002/48197. Buffa R. et al., WO2011/069475A3). In general, it may be stated that, in the great majority of cases, no formation of the respective chloramides was observed in relation to the polysaccharides containing an amide group. The early sources do not mention any presence of hyaluronan chloramide at all (Green S. P. et al., J. Rheumatology, 17, 1670-5, 1990, Lindvall S. et al., Chem.-Biol. Interac. 90, 1-12, 1994, Baker M. S. et al., 461-7 Arthritis and Rheumatism, 32, 4, 1989).

The aforesaid articles describe the examination of the process of degradation of hyaluronan caused by hypochlorous acid or by salts thereof, the latter being formed in a reaction of myeloperoxidase (MPO) with hydrogen peroxide and chlorides. There are several further publications describing the degradation of glycosaminoglycans, mainly those contained in the extracellular matrix, for the purpose of simulating inflammatory processes. The main output should have been constituted by the information concerning both the inflammatory process itself and the expected in vivo presence of certain chemical structures. More recent sources already mention chloramides of hyaluronan.

For example, the publication (Hawkins C. L. et al., *Free Radical Biology & Medicine*, 24, 9, 1396-1410, 1998) deals with the study of the mechanism of degradation of hyaluronic acid, chondroitin sulfate and other substrates, including low-molecular ones, containing an amide group. The used oxidizing agent was HOCl/ClO$^-$. The authors do not assume the existence of other forms of hyaluronan chloramide than an unstable intermediate, which has, however, never been detected in a direct manner. The reason for that lies in its rapid homolytic or reductive cleavage, both cases resulting in the formation of radicals which further react in a way leading to the degradation of the polymer.

Another article (Parsons B. J. et al., *Biochem. J.*, 381, 175-184, 2004) describes the formation of chloramides of hyaluronan, chondroitin sulfate and other substrates utilizing MPO (myeloperoxidase enzyme), hydrogen peroxide and chlorides. The authors assume, that the respective chloramides have a certain lifetime, and provide a detailed description of the degradation of such chloramides utilizing additional agents.

Another very interesting article (Rees M. D. et al., 125, 13719-13733 *J. Am. Chem. Soc.*, 2003) describes the reactions of mono, oligo and polysaccharides containing an amide group with NaClO. The aforesaid article contains a thorough analysis of the stability of chloramides of hyaluronan and of chondroitin sulfate having the modification degrees of 35% and 16%, respectively, both in the presence and in the absence of other reagents and substances, such as $Cu^{2+}$, also in combination with oxygen. It was found out that the degradation is substantially accelerated by the presence of certain metals. A rapid degradation of polymeric chloramides of hyaluronan and of chondroitin sulfate at the temperature of 50° C. was observed even in absence of metals. The degradation was significantly slower at lower temperatures. The results of the direct observations also show that the reaction of MPO with glycosaminoglycans, which takes place in the presence of hydrogen peroxide and in the presence of a physiological amount of chlorides, generates a small amount of glycosaminoglycan chloramides. Accordingly, the authors came to the conclusion that such chloramides are also generated in vivo.

On the basis of the above outputs, it can be concluded that, despite of being known, chloramides of hyaluronan having a low modification degree cannot be expected to have a sufficient stability to make them suitable for preparing any compositions for biomedical applications.

Hyaluronic Acid and Triiodide

The forms of iodine having an oxidation degree higher than −1 (I$^-$) are well-known biocompatible compounds providing antiseptic and disinfecting effects. One of the most widespread forms is triiodide (oxidation degree −⅓) which is subject to reversible decomposition into molecular iodine ($I_2$) and iodide (I$^-$). Molecular iodine is subject to transformation into the gaseous state which means that the solid materials containing triiodide gradually lose their oxidative properties due to the sublimation of $I_2$. For this reason, triiodide is mostly used in the form of various solutions.

An example is the so-called Lugol's iodine solution (aqueous solution of potassium triiodide) that is, owing to its biocompatibility and efficacy, suitable for a wide variety of applications requiring antiseptic or disinfecting effects. A slight disadvantage of the aforesaid solution consist in that it may cause the formation of scars and temporary skin discolourations. The latter drawbacks have been overcome by the addition of hyaluronic acid that noticeably suppresses scarring and, in general, significantly contributes to the healing processes.

The document CZ Pat. No. 12015 describes a composition for preventing bandage adhesions, said composition comprising a physiologically acceptable salt of hyaluronic acid having a molecular weight ranging between 200,000 and 2,500,000 g.mol$^{-1}$, iodine and potassium iodide. The composition, which is available in the form of a sterile aqueous solution or a gel, is able to accelerate the wound healing process. The use of the aforesaid solution of hyaluronic acid and potassium triiodide (under the trade name Hyiodine®) in topical wound healing applications was also described in several publications (Bezdekova B. et al., *Veterinarstvi* 54, 516-519, 2004; Frankova J. et al., *Journal of Materials Science: Materials in Medicine* 17, 891-898, 2006; Slavkovsky R. et al. *Clinical and Experimental Dermatology* 35, 4, 373-379, 2010). The authors obtained excellent results in the field of healing chronic wounds mainly owing to the unique combination comprising a biocompatible antimicrobial triiodide and biocompatible hyaluronic acid, the presence of the latter contributing to the healing process.

However, a significant limitation of the applicability of a solution comprising triiodide and a polysaccharide must be taken into account when storage, transport and possible other in situ applications are concerned. On the one hand, the volume of the material (solution) is significantly greater than that of an analogous solid form and, moreover, the possibilities of the in situ application are considerably limited due to the spatial instability of the solution (its diffluence). On the other hand, the scope of the usability of the liquid form is limited by the type of the packing material used since the oxidizing activity of the triiodide makes it very difficult to use other types of packing materials than standard, but brittle silicate-glass for long-term storing.

The effort for providing a solid material containing a polysaccharide along with a triiodide was not successful due to the inherent instability of the triiodide in the absence of a solvent. The presence of a solvent inhibits the sublimation process of the molecular $I_2$ and enables the latter to be re-bound to I$^-$ and to re-assume the triiodide form $I_3^-$. Therefore, the Lugol's iodine solution by itself rapidly loses its active constituent ($I_2$) during the evaporation of the solvent, said constituent sublimating from the solid state. This constitutes an absolutely fundamental problem with regard to the possibility of long-term storage of any final form containing triiodide.

The document CZ Pat. No. 22394 discloses an antimicrobial mixture for facilitating the healing process as well as an antimicrobial dressing for facilitating wound healing. The above mentioned mixture comprises a physiologically active salt of hyaluronic acid and, as the case may be, farther polysaccharides and active antimicrobial substances. Besides that, it comprises an electrolyte, such as potassium iodide. The composition may assume the form of a chemical or physical mixture, the chemical one being advantageously an aqueous solution and the physical one being advantageously a layer of polysaccharidic fibres, the structure of the said layer containing an antimicrobial substance. The wound dressing is suitable for healing superficial wounds. A particular disadvantage of the aforesaid disclosure consists in the indispensable presence of an antimicrobial substance other than triiodide, which entails a risk of a local skin irritation, undesirable toxicity or allergic reaction.

The document CZ Pat. No. 303548 discloses a smart possibility of avoiding the problem associated with the stability of antimicrobial compositions comprising active iodine with an oxidation degree higher than −1. The solution of the above problem consists in that the active iodine is generated not sooner than in situ when iodides react with iodates. Another problem, however, consists in that the used oxidizing agent (an iodate of an alkali metal) exhibits very strong oxidative effects and causes a damage to the tissue if, in the course of the formation of the active iodine, it comes to contact with the tissue before becoming able to react with iodides. In other words, the portion of the composition which ensures the oxidation of iodides to iodine having an oxidation degree higher than −1, is not biocompatible.

BRIEF SUMMARY

An antimicrobial composition is provided. The composition comprises a chloramid of hyaluronic acid or of modified hyaluronic acid. The chloramid has an amidic group (—NH—CO—). The hydrogens of the amidic group are substituted by chlorine atoms according to the structural formula —NCl—CO—. The composition further comprises an iodide. The substitution degree of the hyaluronic acid or of the modified hyaluronic acid by chlorine is in an amount of from 50% to 100%.

The above mentioned drawbacks are eliminated by the technical solution according to the present invention, wherein the preparation of fully biocompatible forms is disclosed, the latter comprising two parts:
1. iodide
2. a biocompatible oxidizing agent The constituents 1 and 2 may be formed as solid ones contained in a single final composition or as liquid ones contained in two separate compositions. In the latter case, iodine having an oxidation degree higher than −1 is generated and released when both constituents are mixed together in the presence of a solvent. The stability of the final composition during storage and transport is ensured in that the active (volatile) iodine having an oxidation degree higher than −1 is formed not sooner than in situ when an aqueous environment is present.

The biocompatible oxidizing agent in the form of the chloramide of hyaluronic acid having a higher modification degree (more than 50%) serves as a generator of the active iodine, the generation of the latter taking place in a rapid reaction with iodides, and simultaneously as a source of active chlorine. Even though chloramides of hyaluronic acid having a lower modification degree (up to 35%) has already been described, the respective disclosures do not propose any practical application thereof for the reasons associated with an unsatisfactory stability. The final composition comprising the constituents 1 and 2 is unique in that it meets all the following requirements at the same:
- full biocompatibility and biodegradability during all of the various phases of the application
- growth inhibition of a wide variety of microorganisms, fungi or viruses (owing to the content of both the active iodine and chlorine)
- favourable effects on healing processes (owing to the presence of hyaluronic acid)
- possibility of preparing a wide variety of forms having a convenient degree of stability In general, the aforesaid combination is desirable in connection with both external and internal applications requiring antibacterial and, simultaneously, biocompatible wound dressings, fillings, anti-adhesive barriers, membranes, pockets or wraps.

The present invention solves the preparation and use of stable, biocompatible and biodegradable compositions containing hyaluronan chloramide and an iodide, which, upon application, provide a broad spectrum of antimicrobial and antiviral effects accompanied by healing effects, owing to the presence of chlorine and iodine having oxidation degrees higher than −1. Furthermore, a wide variety of forms is described, which forms have largely variable surface areas and degradation time.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Figure 1A:
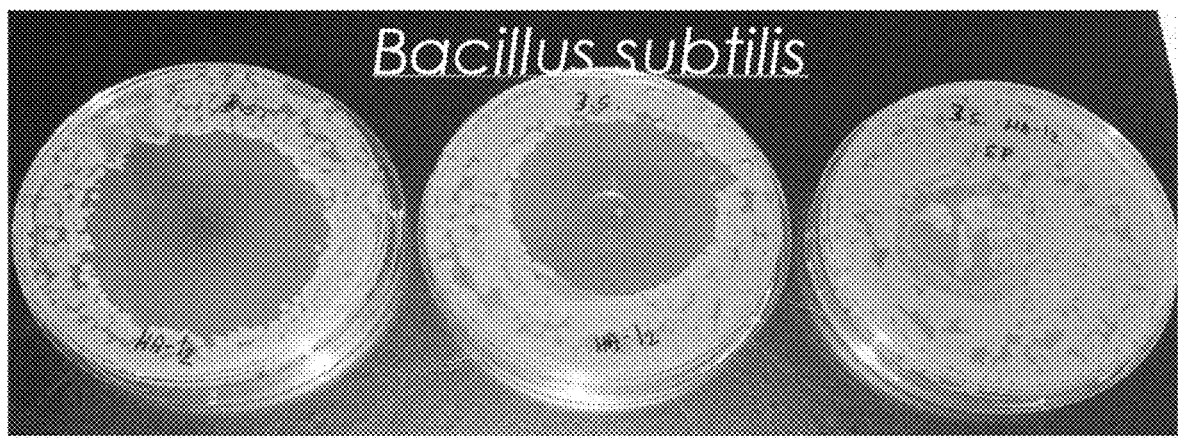
FIG. 1A is a photograph illustrating antimicrobial activity of the composition having the form of a lyophilisate on the basis of hyaluronan chloramide and potassium iodide as prepared according to Example 20.
Figure 1A:
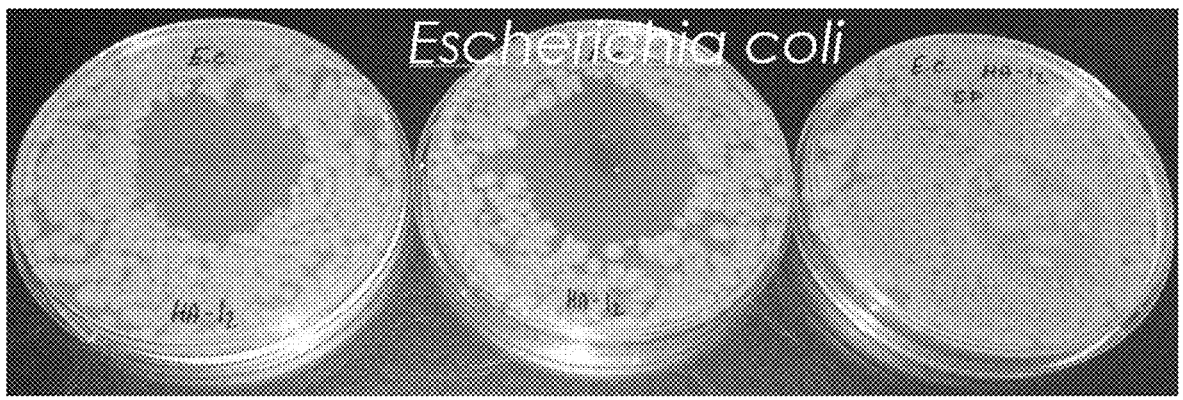
Figure 1A:
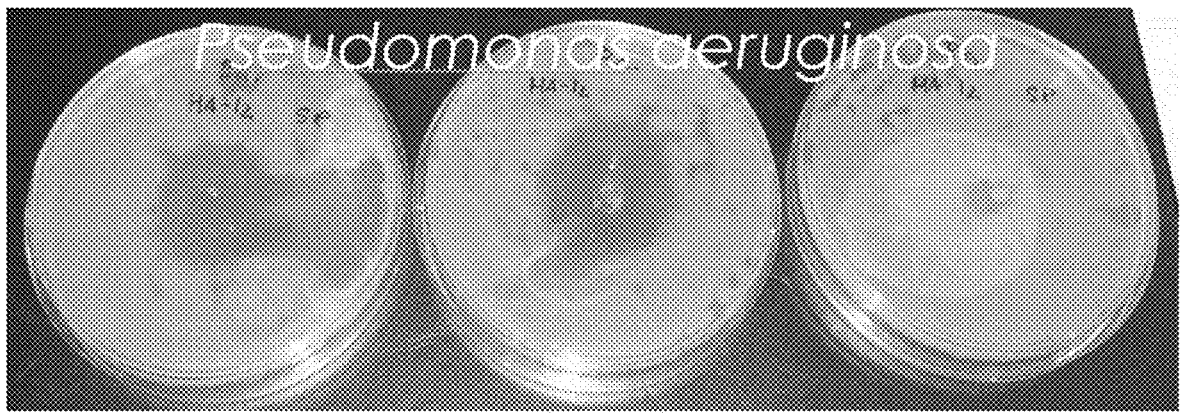

The subject matter of the present invention are compositions containing an iodide and a derivative of hyaluronic acid, in which the majority of the hydrogen atoms contained in the amidic group —NH—CO— is substituted by chlorine atoms —NCl—CO—, the term "majority" referring to the range from 50 to 100%. After having been modified in the above manner, the polymer, namely hyaluronan chloramide, which is present in the form of a solution, rapidly reacts with iodides (the other part of the composition) which results in the formation of iodine compounds with oxidation degrees higher than −1, such as $I_3^-$ or $I_2$, and the native hyaluronic acid. The reaction can be described by the following schema.

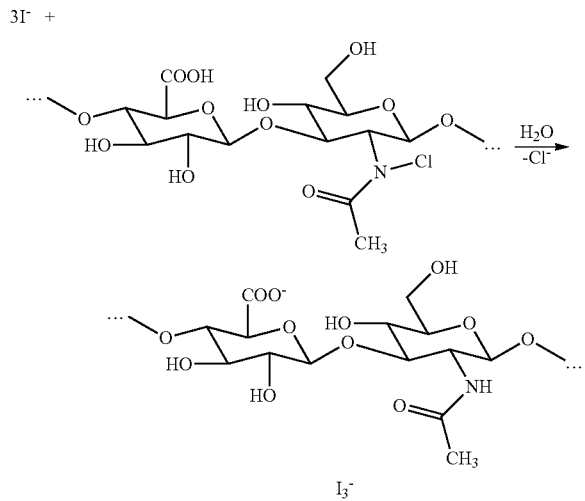

The final compositions may also comprise modified hyaluronic acid, the chemical modification involving the carboxyl and/or hydroxyl groups of the latter.

The derivative of hyaluronic acid may also be represented by a chloramide of modified hyaluronic acid, wherein the hydrogens of the amidic group —NH—CO— are substituted by chlorine atoms according to the structural formula —NCl—CO—, and simultaneously some of the —OH groups of chloramide are replaced by a —O—CO—$R^2$ group and/or some of the —$CH_2$—OH groups are replaced by a —CH=O group and/or some of the CO—OH groups are replaced by a —CO—$OR^2$ group, wherein $R^2$ is a linear or aromatic chain containing $C_1$-$C_{17}$ atoms. The examples of the chloramides of modified hyaluronic acid include ethyl ester, benzyl ester, lauroyl, formyl, palmitoyl or hexanoyl hyaluronan. In certain embodiments, the iodide is selected from the group comprising sodium iodide, potassium iodide, calcium iodide, magnesium iodide and a mixture thereof. In various embodiments, the polysaccharide, i.e. chloramide, has a molecular weight ranging from 5 to 500 kg.$mol^{-1}$. In various embodiments, the molar ratio of the chloramide to the iodide in the composition is within the range from 1:1 to 1:5.

The antimicrobial composition may also comprise an additive in the concentration of up to 90% w/w, said additive being selected from the group comprising polyethylene oxide, water, glycerol, hyaluronic acid, chondroitin sulfate, ester forms of modified hyaluronic acid, aldehyde forms of modified hyaluronic acid, sodium alginate, oxy-cellulose, carboxymethyl cellulose, hydroxyethyl cellulose, esters of fatty acids, sodium chloride, potassium chloride, or calcium chloride. Accordingly, the aforesaid modified hyaluronic acid is hyaluronic acid in which some of the —OH groups are replaced by a —$OCOR^2$ group and/or some of the —$CH_2$—OH groups are replaced by a —CH=O group and/or some of the CO—OH groups are replaced by a —CO—$OR^2$ group, wherein $R^2$ is a linear or aromatic chain containing $C_1$-$C_{17}$ atoms.

The preparation of hyaluronan chloramide takes place utilizing agents containing chlorine bound to nitrogen, in certain embodiments, utilizing trichloroisocyanuric acid or utilizing salts of dichloroisocyanuric acid. The preparation (modification) is carried out in water, the pH value of the solution being within the range from 2.5 to 7.5, in various embodiments, within the range from 4.0 to 6.0. The lower pH value is obtained by adding acetic acid in the amount between 0.2 and 7 eq., in various embodiments, between 2 and 4 eq. The initial substrate can be constituted by hyaluronic acid or by a chemically modified derivative thereof, the molecular weight of such substrate ranging from 40 to 2200 kg.$mol^{-1}$. Furthermore, the preparation of the final compositions comprises the formation of:

solid forms containing iodides and hyaluronan chloramide, such forms including, for example, self-supporting films, lyophilisates, layers of staple fibres (non-woven fabrics), endless fibres, woven fabrics, knitted fabrics, braided fabrics or nanofibrous layers, all of them optionally with a content of farther additives, the proportion of the chloramide in the final composition, calculated in terms of the dry matter, being within the range of 10 to 90% and the proportion of the iodide, calculated in terms of the dry matter, being within the range of 10 to 90%, the solid form being possibly composed of two or more different layers pressed together;

liquid and gel forms, optionally containing further additives, wherein the constituent containing iodides is separated from that containing hyaluronan chloramide, said constituents being mixed together immediately prior to the final application, the proportion of the chloramide in the final composition, calculated in terms of the dry matter, being within the range of 10 to 90% and the proportion of the iodide in the final composition, calculated in terms of the dry matter, being within the range of 10 to 90%.

Furthermore, the invention relates to the use of the final composition, particularly in the fields where the following properties or any combinations of the following properties are required:

oxidative or antimicrobial or antifungal or antiviral activity biocompatibility and biodegradability possibility of preparing various forms having a convenient degree of stability a significant contribution to the healing process controlled biodegradation rate The final composition is usable in biomedical applications, particularly for the preparation of wound dressings, implantable medical devices, preparations against acne, antibacterial fillings, anti-adhesive barriers, membranes, pockets, wrappings, products for the prevention of adhesion following to anastomoses, products for prevention of wound dehiscences, or, in combination with other substances, products for supporting surgical corrections of abdominal wall defects.

A controlled biodegradation rate of the final composition can be achieved either by combining the hyaluronan chloramide with additives exhibiting a slower degradability, such as sodium alginate or carboxymethyl cellulose, and/or by cross-linking the hyaluronan chloramide itself utilizing, for example, polyvalent $Ca^{2+}$ cations.

The present invention relates to the preparation and use of stable, biocompatible and biodegradable compositions containing iodides, such as potassium iodide, sodium iodide, calcium iodide or magnesium iodide, or a mixture thereof, along with a hyaluronan chloramide, which compositions exhibit antimicrobial and antiviral effects accompanied by healing effects. Furthermore, a wide range of forms is described, which forms have largely variable surface areas, mechanical or rheological properties and degradation periods.

The practical implementation of the technical solution according to the present invention is not complicated from the technological viewpoint and does not require any less available chemicals, solvents or isolation procedures to be used.

In the presence of water, the aforesaid mixture generates iodine having an oxidation degree higher than −1 and providing a broad-spectrum antimicrobial effects. The final compositions include numerous forms, such as such a thin film, a lyophilisate, a layer of staple fibres, an endless fibre, woven fabric, knitted fabric, braided fabric or a nanofibrous layer, such that iodide and hyaluronan chloramide can be transferred both into medical devices or into medicaments.

Figure 1B:
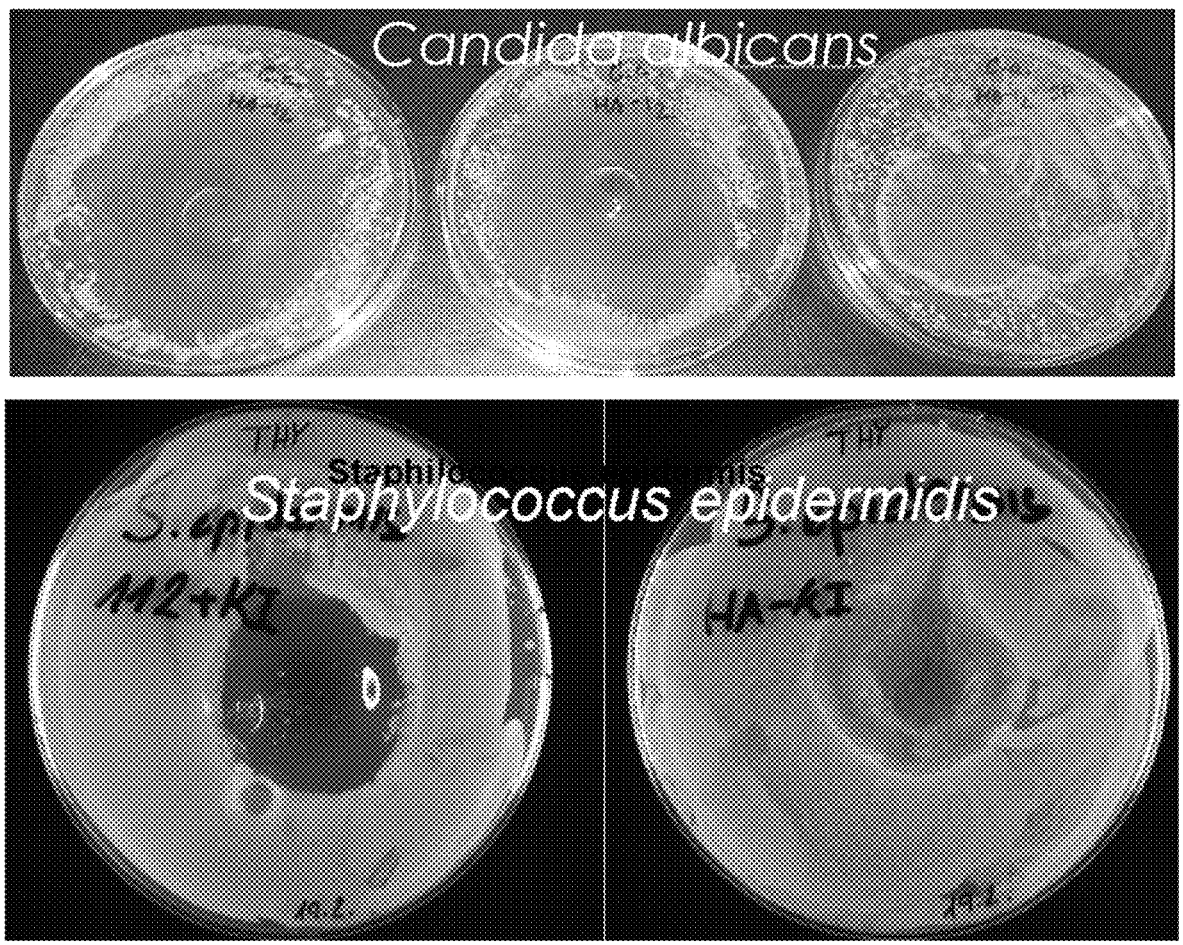
FIG. 1B is a photograph illustrating antimicrobial activity of the composition having the form of a lyophilisate on the basis of hyaluronan chloramide and potassium iodide as prepared according to Example 20.

Furthermore, the invention relates to the use of the final compositions containing an iodide and hyaluronan chloramide in the fields where the following properties or any combinations of the following properties are required:

oxidative or antimicrobial or antifungal or antiviral activity biocompatibility and biodegradability possibility of preparing various forms having a convenient degree of stability a significant contribution to the healing process The figures show the growth inhibition of the microorganisms *Bacillus subtilis, Escherichia coli, Pseudomona aeruginosa, Candida albicans* (all of them in FIG. 1A) and *Staphylolococus epidermidis* (FIG. 1B) in the presence of a composition containing a combination of soluble lyophilisates on the basis of hyaluronan chloramide and soluble lyophilisates on the basis of the mixture of hyaluronan and a potassium iodide in the ratio of 5/1, prepared according to Example 20 (two repeats: the left-hand and middle schemes), in comparison to the control material (the right-hand scheme), namely to the lyophilized native hyaluronic acid supplemented with potassium iodide in the ratio of 5/1 according to Example 19. FIG. 1B shows the comparison between one repeat (the left-hand scheme) and the control material (the right-hand scheme).

The procedure of determining the antimicrobial activity is described in Example 43.

EXAMPLES

DS=degree of substitution=100%*(the molar amount of modified polymer units)/(the total molar amount of all polymer units)

Unless otherwise specified, the expression "equivalent" (eq) as used herein refers to a repeating unit of the respective polysaccharide, such as a dimer of hyaluronic acid. Unless otherwise specified, percentages are weight percents. As used herein, the molecular weight of polymers refers to a weight average value determined utilizing the SEC-MALLS method.

Example 1

Preparation of an Ethyl Ester of Hyaluronan

NaOH was added to the aqueous hyaluronan solution (1 g, 300 kg.mol$^{-1}$, in 40 ml of water) until reaching the pH value of 9. Subsequently, 20 ml of dimethyl sulfoxide and 0.08 ml of ethyl iodide were added and the resulting mixture was stirred at the temperature of 45° C. for 3 days. Afterwards, the resulting mixture was precipitated by 140 ml of 100% isopropanol and the solid matter separated by filtration was washed with isopropanol and vacuum dried. The product (897 mg) was analysed utilizing NMR.
The DS value of the ester was 6% (determined utilizing NMR, lit. Kettou S. et al., PV 2009-399).

Example 2

Preparation of a Benzyl Ester of Hyaluronan

NaOH was added to the aqueous hyaluronan solution (1 g, 300 kg.mol$^{-1}$, in 40 ml of water) until reaching the pH value of 9. Subsequently, 20 ml of dimethyl sulfoxide and 0.08 ml of benzyl bromide were added and the resulting mixture was stirred at the temperature of 20° C. for 4 days. Afterwards, the resulting mixture was precipitated by 140 ml of 100% isopropanol and the solid matter separated by filtration was washed with isopropanol and vacuum dried. The final product (obtained in the amount of 920 mg) was analysed utilizing NMR.
The DS value of the ester was 3% (determined utilizing NMR, lit. Kettou et al., PV 2009-399).

Example 3

Preparation of an Lauroyl of Hyaluronan 70 ml of tetrahydrofuran, 4 equivalents of triethylamine and 0.1 equivalents of 4-dimethylaminopyridine were added to the solution of hyaluronan (5 g, 250 kg.mol$^{-1}$) in 100 ml of distilled water. Simultaneously, lauric acid (4 equivalents) was dissolved in the mixture consisting of 30 ml of tetrahydrofuran and 7 ml of triethylamine and the obtained solution was supplemented with 4.8 ml of ethyl chloroformate for 15 minutes at 0 to 5° C. The resulting suspension was filtered into the solution of hyaluronan and the reaction mixture was stirred at 20° C. for 5 hours. The resulting solution was precipitated by adding 400 ml of 100% isopropanol and washed with 80% isopropanol and then with 100% isopropanol. Afterwards, the precipitate was dried at 40° C. for 2 days. The substitution degree was determined as 37% utilizing NMR

Example 4

Preparation of a Formyl of Hyaluronan

A one-percent aqueous solution of HA (1 g, 200 kg.mol$^{-1}$) containing NaCl 1%, KBr 1%, N-acetylamino-TEMPO (0.01 eq.) and NaHCO$_3$ (20 eq.) was gradually supplemented with an aqueous solution of NaClO (0.5 eq.) under nitrogen atmosphere. The mixture was stirred at 10° C. for 12 hours, whereupon 0.1 g of ethanol were added. Subsequently, the final mixture was stirred for another 1 hour. The resulting solution was diluted with distilled water to the concentration of 0.2% and dialysed against the mixture (0.1% NaCl, 0.1% NaHCO$_3$) 3 times litres (1× a day) and then against distilled water 7 times 5 litres (2× a day). The final solution was evaporated and analysed.
DS 9% (determined by NMR).

Example 5

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 82% (determined by NMR).

Example 6

Preparation of a Hyaluronan Chloramide 5 g of hyaluronan (Mw 40 kg.mol$^{-1}$) were dissolved in 100 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 83% (determined by NMR).

Example 7

Preparation of a Hyaluronan Chloramide 5 g of hyaluronan (Mw 2200 kg.mol$^{-1}$) were dissolved in 1000 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 72% (determined by NMR).

Example 8

Preparation of a Hyaluronan Chloramide 5 g of hyaluronan (Mw 2200 kg.mol$^{-1}$) were dissolved in 250 ml of distilled water. Subsequently, 0.14 ml of acetic acid (0.2 eq.) were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 53% (determined by NMR).

Example 9

Preparation of a Hyaluronan Chloramide 5 g of hyaluronan (Mw 180 kg.mol$^{-1}$) were dissolved in 250 ml of distilled water. Subsequently, 3 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 83% (determined by NMR).

Example 10

Preparation of a Hyaluronan Chloramide 5 g of hyaluronan (Mw 2200 kg.mol$^{-1}$) were dissolved in 250 ml of distilled water. Subsequently, 5 ml of acetic acid (7 eq.) were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for hours. DS 95% (determined by NMR).

Example 11

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 1.07 g (0.33 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 51% (determined by NMR).

Example 12

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 4.8 g (1.5 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 96% (determined by NMR).

Example 13

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, trichloroisocyanuric acid in the amount of 2.91 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 97% (determined by NMR).

Example 14

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, trichloroisocyanuric acid in the amount of 0.87 g (0.3 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 71% (determined by NMR).

Example 15

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 5 hours. Subsequently, the mixture was precipitated by 2.5 litres of isopropanol and filtered. The solid portion was washed with 2 litres of isopropanol, whereupon it was vacuum dried for 20 hours. DS 52% (determined by NMR).

Example 16

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 48 hours. Subsequently, the mixture was precipitated by 2.5 litres of isopropanol and filtered. The solid portion was washed with 2 litres of isopropanol, whereupon it was vacuum dried for 20 hours. DS 85% (determined by NMR). The NMR solution (7 mg of the product in 0.7 ml of $D_2O$) was measured after another 5 days of standing at 20° C. The DS value was determined as 84%. The solid portion in the form of a powder was left to stand at 20° C. for 100 days and after that the sample was dissolved in $D_2O$. The DS value was determined as 84%.

Example 17

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 5° C. for 72 hours. Subsequently, the mixture was precipitated by 2.5 litres of isopropanol and filtered. The solid portion was washed with 2 litres of isopropanol and vacuum dried for 20 hours. DS 64% (determined by NMR).

Example 18

Preparation of a Hyaluronan Chloramide 5 g of hyaluronan (Mw 2200 kg.mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 40° C. for 5 hours. Subsequently, the mixture was precipitated by 2.5 litres of isopropanol and filtered. The solid portion was washed with 2 litres of isopropanol, whereupon it was vacuum dried for 20 hours. DS 75% (determined by NMR).

Example 19

Preparation of a Lyophilisate Comprising Hyaluronan and Potassium Iodide

A solution of hyaluronan (1 g, Mw 2,200 kg.mol$^{-1}$) in 50 ml of distilled water was mixed together with a solution of 0.2 g of potassium iodide in 5 ml of distilled water and the mixture was stirred for 10 minutes. Thereupon, the final solution was deep frozen at the temperature of −50° C. and lyophilized.

Example 20

Preparation of a Lyophilisate (Hyaluronan Chloramide+Hyaluronan+Potassium Iodide)—Iodine Generator The lyophilisate prepared according to Example 19 in the amount of 15 mg and the lyophilisate prepared according to Example 25 in the amount of 15 mg were placed on each other in a stacked manner (the bottom layer being the lyophilisate according to Example 19) and mechanically pressed together utilizing a smooth glass roller at 20° C., the corresponding pressure being applied for 1 minute. The resulting material was stored under dry conditions.

Example 20a

Preparation of a Lyophilisate (Hyaluronan Chloramide+Hyaluronan+Potassium Iodide)—Iodine Generator The lyophilisate prepared according to Example 19 in the amount of 30 mg and the lyophilisate prepared according to Example 25 in the amount of 3 mg were placed on each other in a stacked manner (the bottom layer being the lyophilisate according to Example 19) and mechanically pressed together utilizing a smooth glass roller at 20° C., the required pressure being applied for 1 minute. The resulting material was stored under dry conditions.

Example 20b

Preparation of a Lyophilisate (Hyaluronan Chloramide+Hyaluronan+Potassium Iodide)—Iodine Generator The lyophilisate prepared according to Example 19 in the amount of 3 mg and the lyophilisate prepared according to Example 25 in the amount of 30 mg were placed on each other in a stacked manner (the bottom layer being the lyophilisate according to Example 19) and mechanically pressed together utilizing a smooth glass roller at 20° C., the required pressure being applied for 1 minute. The resulting material was stored under dry conditions.

Example 21

Preparation of a Self-Supporting Film (Hyaluronan Chloramide+Hyaluronan Lauroyl+Potassium Iodide)—Iodine Generator The self-supporting films prepared according to Examples 31 and 32 were placed on each other in a stacked manner (the bottom layer being hyaluronan lauroyl+potassium iodide) and mechanically pressed together utilizing a smooth glass roller at 20° C., the required pressure being applied for 1 minute. The resulting material was stored under dry conditions.

Example 22

Preparation of a Chloramide of an Ethyl Ester of Hyaluronan 0.5 g of ethyl ester of hyaluronan prepared according to Example 1 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 250 ml of isopropanol and filtered. The solid portion was washed with 0.2 litres of isopropanol, whereupon it was vacuum dried for 20 hours. DS 80% (determined by NMR).

Example 23

Preparation of a Chloramide of an Benzyl Ester of Hyaluronan 0.5 g of benzyl ester of hyaluronan prepared according to Example 2 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 0.25 litres of isopropanol and filtered. The solid portion was washed with 0.2 litres of isopropanol, whereupon it was vacuum dried for 20 hours. DS 78% (determined by NMR).

Example 24

Preparation of a Chloramide of Formyl Hyaluronan 0.5 g of formyl hyaluronan prepared according to Example 4 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 0.25 litres of isopropanol and filtered. The solid portion was washed with 0.2 litres of isopropanol, whereupon it was vacuum dried for 20 hours. DS 75% (determined by NMR).

Example 25

Preparation of a Lyophilized Hyaluronan Chloramide

A solution of 1 g of the hyaluronan chloramide, prepared according to Example 16, in 50 ml of distilled water were, immediately following the homogenization, deep frozen at the temperature of −50° C. and lyophilized. The DS value was determined as 83% utilizing NMR.

Example 26

Preparation of a Lyophilized Chloramide of an Ethyl Ester of Hyaluronan

A solution of 0.2 g of the chloramide of ethyl ester of hyaluronan, prepared according to Example 22, in 10 ml of distilled water were, immediately following the homogenization, deep frozen at the temperature of −50° C. and lyophilized. The DS value was determined as 68% utilizing NMR.

Example 27

Preparation of a Lyophilized Chloramide of a Benzyl Ester of Hyaluronan

A solution of 0.2 g of the chloramide of a benzyl ester of hyaluronan, prepared according to Example 23, in 10 ml of distilled water were, immediately following the homogenization, deep frozen at the temperature of −50° C. and lyophilized. The DS value was determined as 67% utilizing NMR.

Example 28

Preparation of a Non-Woven Fabric from Staple Fibres Made of Hyaluronan Chloramide The preparation of a 2% solution was based on the use of hyaluronan chloramide (Example 14) having the substitution degree of 71% according to NMR. The above constituent was weighed and supplemented with distilled water in order to obtain the required amount. The whole mixture was stirred in a stirring device at room temperature, the set speed of the latter being 500 rpm and the stirring time being 24 hours. The final solution was clear and slightly viscous. The method of preparation of staple fibres is based on the precipitation of a polymer solution in a stream of a mobile coagulation bath containing 100% isopropanol. The solution was dosed at room temperature through extrusion nozzles into a stream of a coagulation bath fed through spinning tubes (1 tube/8 mm diameter), the controlled flow rate of the bath being 1.15 m/s. The formation of staple fibres was obtained utilizing precipitation. The formed fibres were entrained in the bath stream, caught by separation combs and transferred into the maturation bath containing 100% isopropanol. Immediately after entering the maturation bath, the raw fibres were ground up by rotating blades of a mixer, the ratio between the amount of the fibres and that of the bath being 0.5 g/350 ml. The final dispersion of fibres was filtered through a permeable substrate through a filter frame. For the given experiment, a filter frame having the surface area of 64 cm$^2$ was used. After having been filtered, the fibres were carried over onto a drying device utilizing a PAD knitted fabric, said device adapted for the fixation of non-woven fabrics. Prior to being placed onto the drying device, the fibres were freed from the precipitant residues utilizing a roller. The non-woven fabric was dried at the temperature of 40° C. for 30 minutes. The resulting layer was separated from the substrate as a self-supporting layer and weighed utilizing an analytic balance. The areal weight of the fabric was 50.2 g/m$^2$. The substitution degree of the formed non-woven fabric was determined as 64% utilizing NMR.

Example 29

Preparation of a Nanofibrous Layer Comprising Hyaluronan Chloramide

For the purpose of preparation of a nanofibrous layer containing hyaluronic acid, an aqueous solution having the following composition was prepared. The concentration of the hyaluronan chloramide, which had been prepared according to Example 5, in the dry matter was 37.5%, the concentration of the native hyaluronan having the molecular weight of 80 kg.mol$^{-1}$ was 37.5%, and the amount of polyethylene oxide having the molecular weight of 600 kg.mol$^{-1}$ was 25%. The overall concentration of the dry matter was 5%. The solution was transferred into a syringe and spun electrostatically on a plate-type collector using a needleless linear nozzle, the voltage and spacing between the emitter and the collector being 50 kV and 16 cm, respectively. The dimension of the fibres was 110±27 nm. The DS value was determined as 30% utilizing NMR.

Example 29a

Preparation of a Nanofibrous Layer Comprising Hyaluronan and Potassium Iodide

For the purpose of preparation of a nanofibrous layer containing hyaluronic acid, an aqueous solution having the following composition was prepared. The concentration of the native hyaluronan having the molecular weight of 80 kg.mol$^{-1}$ was 62.5%, the amount of polyethylene oxide having the molecular weight of 600 kg.mol$^{-1}$ was 25%, and the amount of KI was 12.5%. The overall concentration of the dry matter was 5%. The solution was transferred into a syringe and spun electrostatically on a plate-type collector using a needleless linear nozzle, the voltage and spacing between the emitter and the collector being 56 kV and 18 cm, respectively. The dimension of the fibres was 140±35 nm.

Example 30

Preparation of a Self-Supporting Film Comprising Hyaluronan Chloramide

The preparation of the film took place in a special drying device where the film was dried in a closed chamber. The apparatus is equipped with the bottom and top plates, the temperatures thereof being controllable. The detailed description of the apparatus is provided in the publication Foglarova et al., PV2015-166; Foglarova M. Et al., *Carbohydrate Polymers* 2016, 144, 68-75. The weighed amount of 200 mg of the hyaluronan chloramide described in Example 5 was dissolved in 20 ml of demineralised water whereupon the resulting solution was stirred for 2 hours. Then the final solution was dosed to the drying device onto a pad (hydrophobized glass) and was dried in a closed chamber for 18 hours. The bottom and top plates of the dryer had the temperatures of 50° C. and 20° C., respectively. After having been dried, the film was released from the pad and kept for future use. The DS value was determined as 60% utilizing NMR.

Example 31

Preparation of a Self-Supporting Film from Hyaluronan and Potassium Iodide (10/1)

The preparation of the film took place in the device described in Example 30. The weighed amount of 160 mg of sodium hyaluronate and 16 mg of potassium iodide was dissolved in 16 ml of demineralised water whereupon the resulting solution was stirred for 15 minutes. Then the final mixed solution was dosed to the drying device onto a pad (hydrophobized glass) and was dried in a closed chamber for 7 hours. The bottom and top plates of the dryer had the temperatures of 50° C. and 20° C., respectively. After having been dried, the film was released from the pad and kept for future use.

Example 32

Preparation of a Self-Supporting Film from Lauroyl Hyaluronan and Hyaluronan Chloramide (3/1)

The preparation of the film took place in the device described in Example 30. The weighed amount of 150 mg of the lauroyl derivative of sodium hyaluronate (as described in Example 3) was dissolved in 15 ml of an aqueous solution of 2-propanol (50% w/w) whereupon the resulting solution was stirred for 18 hours. The weighed amount of 50 mg of the hyaluronan chloramide described in Example 5 was dissolved in 5 ml of demineralised water whereupon the resulting solution was stirred for 2 hours. Subsequently, both the solutions were blended for 30 minutes. Then the final mixed solution was dosed to the drying device onto a pad (hydrophobized glass) and was dried in a closed chamber for 7 hours. The bottom and top plates of the dryer had the temperatures of 50° C. and 20° C., respectively. After having been dried, the film was released from the pad and kept for future use. The DS value of the hyaluronan chloramide in the final material was determined as 25% utilizing NMR.

Example 33

Preparation of a Nanofibrous Layer (Hyaluronan Chloramide+Hyaluronan+Potassium Iodide)—Iodine Generator The nanofibrous layers prepared according to Examples 29 and 29a were placed on each other in a stacked manner (the bottom layer being hyaluronan+potassium iodide). The material was stored under dry conditions.

Example 34

Preparation of a Two-Component Mixture in the Form of a Solution (Hyaluronan Chloramide+Sodium Iodide 1/1)—Iodine Generator Immediately prior to application, a solution of 100 mg of hyaluronan chloramide, as prepared according to Example 5, in 3 ml of distilled water was mixed with a solution comprising 29 mg of sodium iodide in 1 ml of distilled water utilizing a static mixer. Immediately thereafter, orange-coloured triiodide and iodine were formed in the resulting mixture.

Example 35

Preparation of a Two-Component Mixture in the Form of a Gel (Hyaluronan Chloramide+Calcium Iodide 1/5)—Iodine Generator Immediately prior to application, a solution of 100 mg of hyaluronan chloramide, as prepared according to Example 5, in 6 ml of distilled water was mixed with a solution comprising 758 mg of the native hyaluronan having the molecular weight of 1,900 kg.mol$^{-1}$ and 142 mg of calcium iodide in 35 ml of distilled water utilizing a static mixer. Immediately thereafter, orange-coloured triiodide and iodine were formed in the resulting viscous mixture.

Example 36

Preparation of an Oxycellulose/Hyaluronan Chloramide Lyophilizate

A solution of 0.3 g of oxycellulose (Mw 50 kg.mol$^{-1}$) and 0.1 g of the hyaluronan chloramide, prepared according to Example 5, in 100 ml of distilled water were, immediately following the homogenization, deep frozen at the temperature of −50° C. and lyophilized. The DS value of the hyaluronan chloramide was determined as 24% utilizing NMR.

Example 37

Preparation of an Alginate/Hyaluronan Chloramide Lyophilizate

A solution of 0.3 g of alginate (Mw 40 kg.mol$^{-1}$) and 0.1 g of the hyaluronan chloramide, prepared according to Example 5, in 100 ml of distilled water were, immediately following the homogenization, deep frozen at the temperature of −50° C. and lyophilized. The DS value of the hyaluronan chloramide was determined as 26% utilizing NMR.

Example 38

Preparation of a Carboxymethyl Cellulose/Hyaluronan Chloramide Lyophilizate

A solution of 0.3 g of carboxymethyl cellulose (Mw 30 kg.mol$^{-1}$) and 0.03 g of the hyaluronan chloramide, prepared according to Example 5, in 100 ml of distilled water were, immediately following the homogenization, deep frozen at the temperature of −50° C. and lyophilized. The DS value of the hyaluronan chloramide was determined as 3% utilizing NMR.

Example 39

Preparation of a Chondroitin Sulfate/Hyaluronan Chloramide Lyophilizate

A solution of 0.3 g of chondroitin sulfate (Mw 45 kg.mol$^{-1}$) and 0.1 g of the hyaluronan chloramide, prepared according to Example 5, in 100 ml of distilled water were, immediately following the homogenization, deep frozen at the temperature of −50° C. and lyophilized. The DS value of the hyaluronan chloramide was determined as 25% utilizing NMR.

Example 40

Preparation of a Hydroxyethyl Cellulose/Hyaluronan Chloramide Lyophilizate

A solution of 0.3 g of hydroxyethyl cellulose (Mw 35 kg.mol$^{-1}$) and 0.1 g of the hyaluronan chloramide, prepared according to Example 5, in 100 ml of distilled water were, immediately following the homogenization, deep frozen at the temperature of −50° C. and lyophilized. The DS value of the hyaluronan chloramide was determined as 25% utilizing NMR.

Example 41

Preparation of a Formyl Hyaluronan/Hyaluronan Chloramide Lyophilizate

A solution of 0.3 g of hyaluronan formyl (Mw 50 kg. mol$^{-1}$) prepared according to Example 4 and 0.1 g of the hyaluronan chloramide prepared according to Example 5 in 100 ml of distilled water were, immediately following the homogenization, deep frozen at the temperature of −50° C. and lyophilized. The DS value of the hyaluronan chloramide was determined as 25% utilizing NMR.

Example 42

Preparation of a Lyophilizate of Hyaluronan Chloramide Cross-Linked with CaCl$_2$ A solution of hyaluronan chloramide (0.1 g) prepared according to Example 5 in 100 ml of distilled water was supplemented with 0.01 g of CaCl$_2$.2H$_2$O and the mixture was stirred at 20° C. for 1 hour. Following the homogenization, the final viscous solution was deep frozen at the temperature of −50° C. and lyophilized. The DS value of the hyaluronan chloramide was determined as 64% utilizing NMR.

Example 43

In Vitro Antimicrobial Activity Testing (FIGS. 1A and 1B):

For the individual microorganisms subjected to testing, suspensions having the concentration of approximately 10$^5$ CFU/ml were prepared. The suspension in the amount of 100 µl was inoculated on the surface of tryptone soya agar in Petri dishes (an approximate count of microorganisms applied in each dish was 10$^4$ CFU). The suspension was uniformly spread over the entire surface of the dish utilizing a sterile loop. After soaking the suspension in the agar, the surface of agar was covered by sterile square-shaped samples selected for testing. The dishes with the tested bacterium strains were cultivated at 37° C. for 24 hours. The tests involved the lyophilizates of hyaluronan chloramide and potassium iodide prepared according to Example 20, in the form of square pieces having a weight ranging between 25 and 35 mg and approximate dimensions of 15 mm×15 mm, the respective control materials being analogous lyophilisates having no content of hyaluronan chloramide, as prepared according to Example 19. For efficacy testing, the diffusion plate method (2D layout) was selected. For the cultivation, a non-selective substrate (tryptone-soya agar) was selected. The square-shaped samples were tested on the following microorganisms: *Bacillus subtilis, Escherichia coli, Staphylococcus aureus, Candida Albicans, Pseudomona aeruginosa, Staphylococcus epidermidis*. The FIG. 1 clearly shows that the compositions containing hyaluronan chloramide along with an iodide according to the invention provide a significantly higher efficacy in comparison to the control material having no content of hyaluronan chloramide.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-25, ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

The invention claimed is:

1. An antimicrobial composition comprising:
   a chloramide of hyaluronic acid or of modified hyaluronic acid, the chloramide having an amidic group (—NH—CO—), wherein the hydrogens of the amidic group are substituted by chlorine atoms according to the structural formula —NCl—CO—; and
   an iodide;
   wherein the substitution degree of the hyaluronic acid or of the modified hyaluronic acid by chlorine is in an amount of from 50% to 100%.

2. The antimicrobial composition according to claim 1, wherein the chloramide has an —OH group, a —CH$_2$—OH, and a —CO—OH group, and wherein:
- (A) at least a portion of the —OH groups of chloramide are substituted by a —O—CO—R$^2$ group, where R$^2$ is a C$_1$-C$_{17}$ linear or aromatic group;
- (B) at least a portion of the —CH$_2$—OH groups are substituted by a —CH=O group;
- (C) at least a portion of the —CO—OH groups are substituted by a —CO—OR$^2$ group, where R$^2$ is a C$_1$-C$_{17}$ linear or aromatic group; or
- (D) any combination of (A), (B), and (C).

3. The antimicrobial composition according to claim 1, wherein the chloramide is of modified hyaluronic acid, the modified hyaluronic acid is selected from the group of ethyl ester, benzyl ester, lauroyl, formyl, palmitoyl, hexanoyl hyaluronan, and combinations thereof, and the iodide is selected from the group of sodium iodide, potassium iodide, calcium iodide, magnesium iodide, and combinations thereof.

4. The antimicrobial composition according to claim 1, wherein the molecular weight of the chloramide is within the range of 5 to 500 kg.mol$^{-1}$.

5. The antimicrobial composition according to claim 1, wherein the molar ratio of the chloramide to the iodide in the composition is within the range of 1:1 to 1:5.

6. The antimicrobial composition according to claim 1, further comprising an additive in an amount of no greater than 90 wt. % based on total weight of the composition.

7. The antimicrobial composition according to claim 6, wherein the additive is selected from the group of water, sodium chloride, calcium chloride, glycerol, hyaluronic acid, chondroitin sulfate, sodium alginate, oxy-cellulose, carboxymethyl cellulose, hydroxy ethyl cellulose, a modified hyaluronic acid, and combinations thereof, with the proviso that when the additive comprises a modified hyaluronic acid;
- (A) at least a portion of the —OH groups of modified hyaluronic acid are substituted by a —O—CO—R$^2$ group, where R$^2$ is a C$_1$-C$_{17}$ linear or aromatic group;
- (B) at least a portion of the —CH$_2$—OH groups are substituted by a —CH=O group;
- (C) at least a portion of the —CO—OH groups are substituted by a —CO—OR$^2$ group, where R$^2$ is a C$_1$-C$_{17}$ linear or aromatic group; or
- (D) any combination of (A), (B), and (C).

8. The antimicrobial composition according to claim 1, wherein the composition is in the form of a solid substrate selected from the group of a self-supporting film, lyophilisate, a layer of staple fibres, an endless fibre, a woven fabric, knitted fabric, braided fabric, a layer of nanofibers, and combinations thereof, and wherein the content of the chloramide in the composition, calculated in terms of the dry matter, is within the range of from 10 to 90%.

9. The antimicrobial composition according to claim 8, wherein the composition is in the form of a solid substrate composed of two or more layers.

10. The antimicrobial composition according to claim 1, wherein the composition is in the form of two separate solutions or gels adapted to be mixed immediately before the application of the composition, wherein the chloramide of hyaluronic acid or chloramide of the modified hyaluronic acid is comprised in the first solution or gel, and the iodide is comprised in the second solution or gel, wherein the content of the chloramide in the composition, calculated in terms of dry matter, is within the range of from 10 to 90% and the content of the iodide in the composition, calculated in terms of dry matter, is within the range of from 10 to 90%.

11. The antimicrobial composition according to claim 1, utilized for the preparation of wound covers or for the preparation of implantable medical devices, preparations against acne, antibacterial fillings, antiadhesive barriers, membranes, pouches, or wrappings.

* * * * *